US008189185B2

(12) United States Patent
Soeda et al.

(10) Patent No.: US 8,189,185 B2
(45) Date of Patent: *May 29, 2012

(54) OPTICAL INSPECTION METHOD AND OPTICAL INSPECTION SYSTEM

(75) Inventors: Hideki Soeda, Hitachinaka (JP); Masayuki Ochi, Kamisato (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 12/963,416

(22) Filed: Dec. 8, 2010

(65) Prior Publication Data

US 2011/0075139 A1    Mar. 31, 2011

Related U.S. Application Data

(63) Continuation of application No. 12/163,137, filed on Jun. 27, 2008, now Pat. No. 7,869,025.

(30) Foreign Application Priority Data

Jun. 28, 2007 (JP) ................................. 2007-170682
Jan. 16, 2008 (JP) ................................. 2008-006772

(51) Int. Cl.
*G01N 21/00*    (2006.01)

(52) U.S. Cl. ..................................................... 356/237.5

(58) Field of Classification Search ........................ None
See application file for complete search history.

(56) References Cited

U.S. PATENT DOCUMENTS

| 6,798,504 B2 | 9/2004 | Sato et al. |
| 7,528,942 B2 | 5/2009 | Nakano et al. |
| 7,869,025 B2 * | 1/2011 | Soeda et al. ............... 356/237.5 |
| 2006/0068512 A1 | 3/2006 | Ohshima et al. |
| 2008/0059094 A1 | 3/2008 | Shimura et al. |

FOREIGN PATENT DOCUMENTS

| JP | 9-304289 | 11/1997 |
| JP | 11-64234 A | 3/1999 |
| JP | 2002-98645 A | 4/2002 |
| JP | 2006-17630 | 1/2006 |
| JP | 2006-201044 | 8/2006 |
| JP | 2006-201179 | 8/2006 |
| JP | 2007-033433 A | 2/2007 |
| JP | 2007-302997 | 11/2007 |

OTHER PUBLICATIONS

Japanese Office Action, w/ partial English translation thereof, issued in Japanese Patent Application No. 2008-006772, dated Feb. 28, 2012.

* cited by examiner

*Primary Examiner* — Gregory J Toatley
*Assistant Examiner* — Amanda Merlino
(74) *Attorney, Agent, or Firm* — McDermott Will & Emery LLP (57) ABSTRACT

An optical semiconductor wafer inspection system and a method thereof are provided for voids and particles produced in a flattening process by classifying and inspecting defects such as scratches, a polishing or grinding technique used for semiconductor manufacturing. The present invention is an optical semiconductor wafer inspection system and a method thereof characterized by obliquely illuminating a scratch, void or particle produced on the surface of a polished or ground insulating film at substantially the same velocity of light, detecting scattered light at the time of oblique illumination from the surface of an inspection target at different angles and thereby classifying the scratch, void or particle.

24 Claims, 8 Drawing Sheets

SCATTER DIAGRAM OF LUMINOUS INTENSITY RATIO BETWEEN PARTICLE AND VOID

FIG.7

$\theta 1$ = ANGLE OF INCIDENCE

$n1 \cdot \sin\theta 1 = n2 \cdot \sin\theta 2$ $$\text{P-WAVE (Rp)} = \left| \frac{n_I \cos\theta_I - n_{II} \cos\theta_{II}}{n_I \cos\theta_I + n_{II} \cos\theta_{II}} \right|^2$$

$$\text{S-WAVE (Sp)} = \left| \frac{n_I \cos\theta_{II} - n_{II} \cos\theta_I}{n_I \cos\theta_{II} + n_{II} \cos\theta_I} \right|^2$$

RELATIONAL EXPRESSION BETWEEN REFLECTION FACTOR
AND ANGLE OF INCIDENCE OF LIGHT

FIG.8

GRAPH OF REFLECTION FACTOR ON INTERFACE BETWEEN MATTER AND AIR

FIG.9

STATE OF VOID SCATTERED LIGHT

FIG.10

STATE OF PARTICLE SCATTERED LIGHT

OPTICAL INSPECTION METHOD AND OPTICAL INSPECTION SYSTEM

CROSS-REFERENCE TO RELATED APPLICATIONS

This application is a Continuation of U.S. application Ser. No. 12/163,137, filed on Jun. 27, 2008, now U.S. Pat. No. 7,869,025, claiming priority of Japanese Patent Application No. 2007-170682, filed on Jun. 28, 2007 and Japanese Patent Application No. 2008-006772, filed on Jan. 16, 2008, the entire contents of each of which are hereby incorporated by reference.

BACKGROUND OF THE INVENTION AND RELATED ART STATEMENT

The present invention relates to an optical semiconductor wafer inspection system and a method thereof for classifying and inspecting a defect such as scratch, void or particle as an example of extraneous material produced in a flattening process with a polishing or grinding processing technique used during semiconductor manufacturing.

As a conventional technique for classifying and inspecting defect such as scratch and particle on a semiconductor wafer, there is known a technique described in JP-A-2006-201179. That is, the technique described therein combines a high-angle detection optical system and middle-angle detection optical system which condense and receive scattered light generated from locations illuminated by a right-overhead illumination system and oblique illumination system and convert the scattered light to a luminous intensity signal, thereby sets a plurality of detection conditions and classifies defects on an inspection target based on a relationship between luminous intensity signals detected under the respective conditions.

Patent Document 1: JP-A-2006-201179

BRIEF SUMMARY OF THE INVENTION

However, the above described conventional technique necessarily needs to be switched between the right-overhead illumination system and oblique illumination system as for the illumination system as the plurality of detection conditions and does not consider fixing the illumination system to the oblique illumination system and switching between the high-angle detection optical system and middle-angle detection optical system or between the high-angle detection optical system and low-angle detection optical system.

Therefore, the conventional technique does not consider carrying out processes by the high-angle detection optical system and low-angle detection optical system in parallel and increasing the inspection speed either. Here, the "middle-angle" and "low-angle" do not mean absolute angles but mean relative positions of angles lower than the position of high-angle.

It is an object of the present invention to solve the above described problems and provide an optical inspection system and an optical inspection method capable of speedily classifying defect such as scratch, void or particle which exists on the surface of an inspection target such as a semiconductor wafer.

In order to attain the above described object, the present invention provides an optical inspection method for an optical inspection system including a stage on which an inspection target is placed, an oblique illumination system that obliquely illuminates a surface of the inspection target placed on the stage, a high-angle detection optical system that directs light toward the surface at a high angle and detects high-angle scattered light generated from the inspection target with oblique illumination, and a low-angle detection optical system that directs light toward the surface at a low angle and detects low-angle scattered light generated from the inspection target with oblique illumination, wherein luminous intensity detected by the high-angle detection optical system is compared with luminous intensity detected by the low-angle detection optical system to classify a defect which exists on the inspection target.

The present invention provides an optical inspection system including a stage on which an inspection target is placed, an oblique illumination system that obliquely illuminates a surface of the inspection target and a detection optical system that detects scattered light generated from the inspection target through illumination by the oblique illumination system, wherein the detection optical system includes a high-angle detection optical system that directs light toward the surface at a high angle and a low-angle detection optical system that directs light toward the surface at a low angle, and a judgment section that compares luminous intensity detected by the high-angle detection optical system with luminous intensity detected by the low-angle detection optical system and classifies a defect on the inspection target.

The present invention can speedily inspect defects.

Other objects, features and advantages of the invention will become apparent from the following description of the embodiments of the invention taken in conjunction with the accompanying drawings.

DETAILED DESCRIPTION OF THE INVENTION

Embodiments of an optical semiconductor wafer inspection system and a method thereof aimed at stable operation of a flattening process used in a semiconductor manufacturing process according to the present invention will be explained with reference now to the attached drawings.

Figure 2:
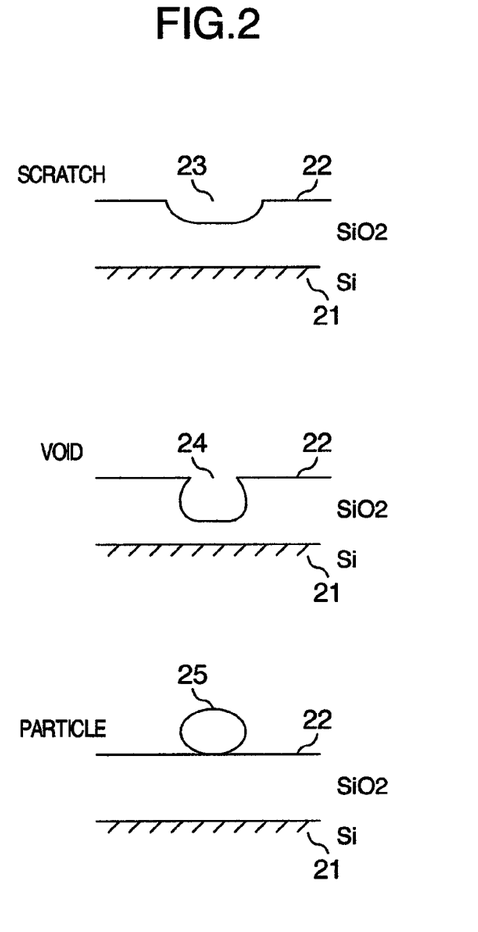
FIG. 2 shows examples of defects to be classified according the embodiment of the present invention.

As shown in FIG. 2, when forming an SiO2 film (processing target) 22 on an Si wafer 21 and applying CMP (Chemical Mechanical Polishing), this embodiment classifies a scratch 23, void 24 and particle 25 generated on a wafer 10.

However, the Si substrate 21 does not always exist below the SiO2 film 22, but a wiring layer may exist instead.

In the CMP process, polishing is performed to flatten the surface of this SiO2 film 22. Therefore, the scratch 23 which is a polishing scar is produced on the surface of the SiO2 film 22 as shown in FIG. 2.

Furthermore, the void 24 corresponds to a bubble (void) existing inside the SiO2 film 22 that emerges when the surface is polished. The particle 25 may be dust generated from within a semiconductor manufacturing system stuck to the surface of the SiO2 film 22.

For a stable operation of the flattening process in this way, it is important to quickly carry out a defect classification process simultaneously with detection of defects, estimate the mechanism of occurrence of defects and take remedial actions.

Figure 1:
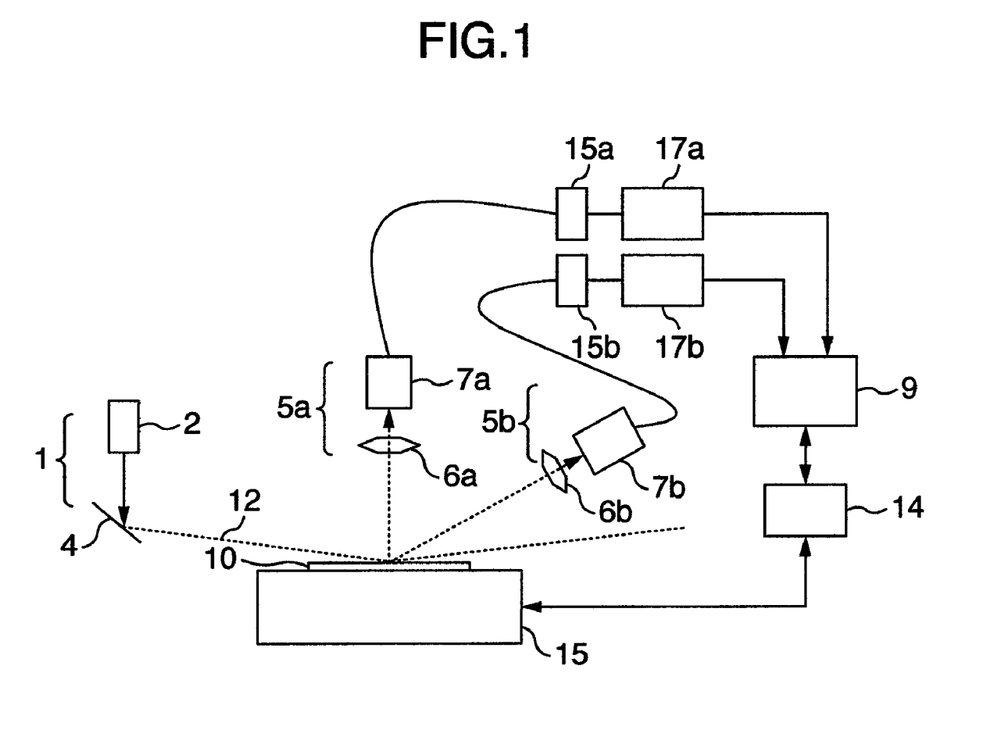
FIG. 1 is a configuration example of an inspection system according an embodiment of the present invention.

Next, FIG. 1 shows an example of the optical semiconductor wafer inspection system to implement the embodiment.

The optical semiconductor wafer inspection system includes a wafer 10 which is an inspection target placed on a stage 15, position coordinates of which are measured and traveling in the XY direction of which is controlled, a light source 2 made up of, for example, an Ar laser having a wavelength of 488 nm and an oblique illumination optical system 1 made up of a reflecting mirror 4.

Furthermore, the optical semiconductor wafer inspection system has a high-angle detection optical system 5a and a low-angle detection optical system 5b made up of condensing lenses 6a, 6b, photoelectric transducers 7a and 7b made up of a photomultiplier, CCD camera, CCD sensor and TDI sensor or the like respectively and A/D converters 15a and 15b that convert analog luminous intensity signals outputted from the photoelectric transducers 7a and 7b to digital luminous intensity signals.

The optical semiconductor wafer inspection system further has a stage controller 14 that controls the traveling of the stage 15 based on the position coordinates measured from the stage 15, judgment sections 17a and 17b that detect defects in synchronization with the traveling of the stage 15 and calculates luminous intensity signals thereof, and an overall control section 9 that controls the stage controller 14, further controls the judgment sections 17a and 17b and receives inspection results obtained from the judgment sections 17a and 17b.

Examples of the judgment sections 17a and 17b include dedicated digital signal circuits that can perform pipeline processing in synchronization with scan clocks of the photoelectric transducers 7a and 7b that perform scanning in synchronization with the traveling of the stage 15.

Instead of performing the above described synchronization processing as the judgment sections 17a and 17b, there is also a method of storing the outputs of the A/D converters 15a and 15b in a memory and performing processing asynchronously, for example. In this case, the inspection speed is slower than the synchronous processing.

The illumination optical system and detection optical system will be explained by quoting FIG. 4.

Figure 4A:
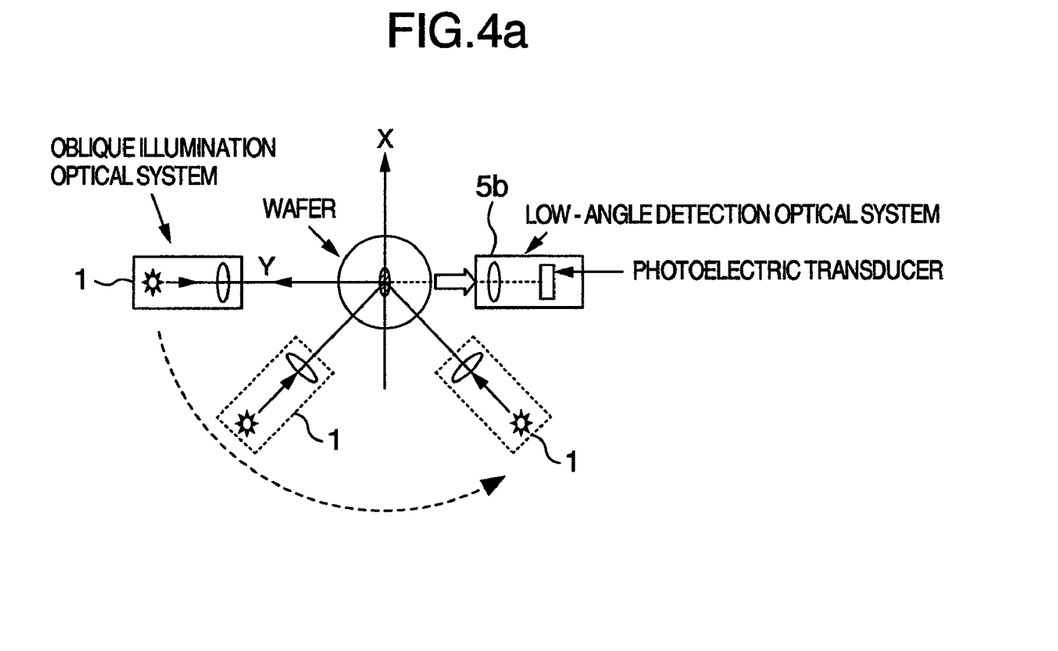
FIGS. 4a and 4b show examples of an illumination optical system and a detection optical system according the embodiment of the present invention.

FIG. 4(a) is a plan view of the arrangement of the illumination optical system and detection optical system seen from right above.

The low-angle detection optical system 5b having a low angle is located at 180° with respect to the Y axis (minus direction: counterclockwise direction). The oblique illumination optical system 1 can be changed in three directions of 0°, 45° and 135° with respect to the Y axis.

In other words, the positional relationship between the low-angle detection optical system and oblique illumination system is arbitrarily selectable within a range except 0° to 45° within the XY plane on the surface.

Figure 4B:
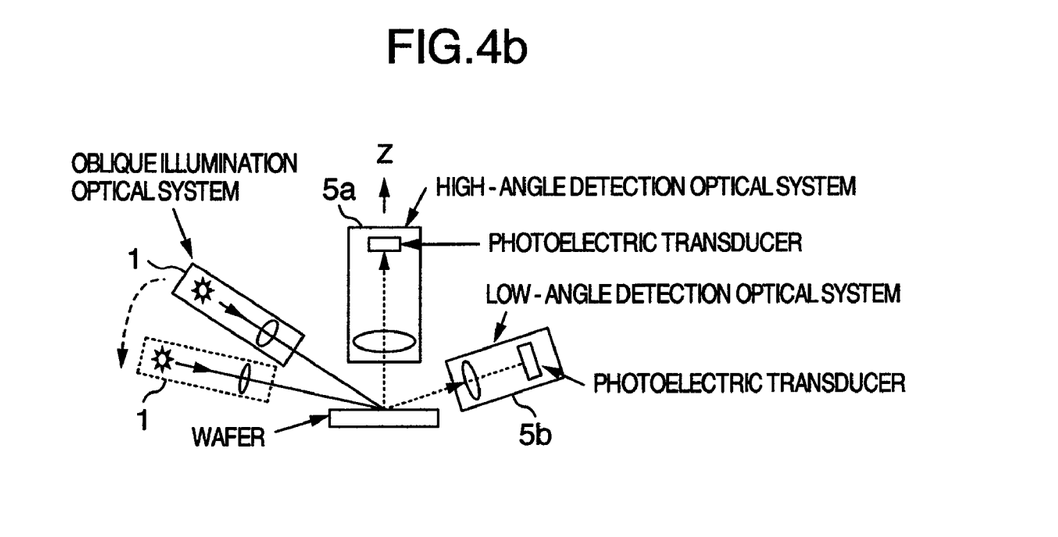

FIG. 4(b) is a front view of the arrangement of the illumination optical system and detection optical system seen from right abeam.

The high-angle detection optical system 5a is located at 90° with respect to the XY plane. The low-angle detection optical system 5b is located at 12° with respect to the XY plane. The oblique illumination optical system 1 can be changed in three directions of 3°, 5° and 20° with respect to the X axis. YAG laser 355 nm can be used for the inclined illumination wavelength.

In other words, the oblique illumination system is arbitrarily selectable within a range of angle of elevation of 3° to 20° with respect to the XY plane (on the surface).

Furthermore, the low-angle detection optical system is kept to an angle of elevation of approximately 12° with respect to the XY plane (on the surface).

Next, the detection procedure will be explained.

Oblique illumination light 12 is irradiated onto the CMP plane of an insulating film 22 on the wafer 10 so as to prevent the oblique illumination light 12 from being directly irradiated onto the surfaces of the condensing lenses 6a and 6b and prevent regularly reflected light of the oblique illumination light 12 from the wafer 10 from being directly irradiated onto the surfaces of the condensing lenses 6a and 6b.

While eliminating the regularly reflected light component generated from the insulating film 22, only the scattered light (low-order diffracted light component) emitted from the scratch 23, void 24 or particle 25 as the defect on the insulating film 22 is condensed by the condensing lenses 6a and 6b onto the light-receiving surfaces of the photoelectric transducers 7a and 7b made up of a CCD, a TDI sensor or the like. While moving the stage 15, the photoelectric transducers 7a and 7b such as a CCD and a TDI sensor are made to scan.

The outputs of the photoelectric transducers 7a and 7b are A/D-converted by the A/D converters 16a and 16b in synchronization with the scanning of the photoelectric transducers 7a and 7b such as a CCD and a TDI sensor.

The outputs of the A/D converters 16a and 16b are inputted to the judgment sections 17a and 17b and the judgment sections 17a and 17b calculate scattered light luminous intensity information and defect position information from the scratch 23, void 24 or particle 25 as the defect on the insulating film 22 in synchronization with the movement of the stage 15 and the scanning of the photoelectric transducers 7a and 7b and record the information in the overall control section 9 as the inspection result.

As the method of judging a defect, the existence of a defect is judged, for example, when the luminous intensity level of the scattered light from the insulating film 22 is a certain threshold or above.

Next, classification after the existence of a defect is judged will be explained.

Figure 3:
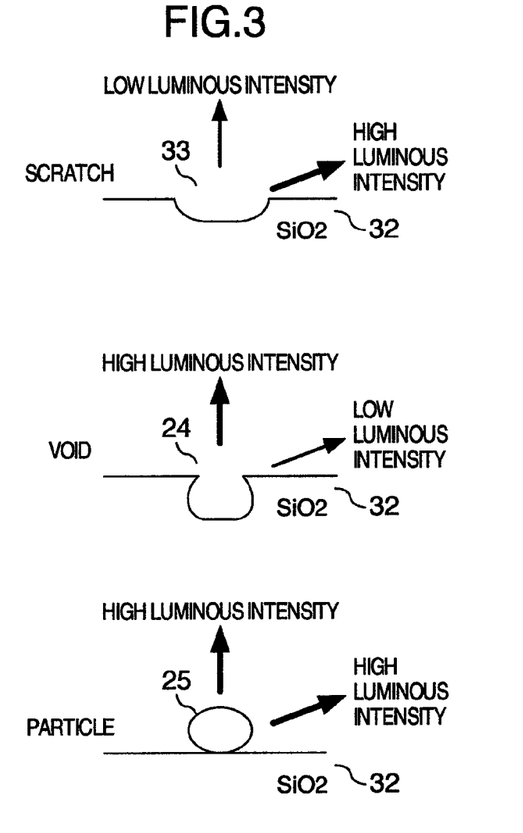
FIG. 3 shows examples of a defect classification method according the embodiment of the present invention.

The principle of classification for implementing the above described embodiment according to the present invention will be explained using FIG. 3.

In the case of the scratch 33 which is a defect on the insulating film 32, since this is a shallow concave defect, the luminous intensity signal of the high-angle detection optical system 5a is smaller than the low-angle detection optical system 5b irrespective of the defect size.

In the case of the void 34, since this is a deep concave defect, exposure at the edge of the hole seen from the direction of the low-angle detection optical system 5b is small and the luminous intensity signal of the high-angle detection optical system 5a is larger than the low-angle detection optical system 5b irrespective of the defect size.

In the case of the particle 25, since this is a high convex defect, the luminous intensity signal of the high-angle detection optical system 5a is substantially the same as the luminous intensity signal of the low-angle detection optical system 5b irrespective of the defect size.

Therefore, it is possible to classify the scratch 33, void 34 and particle 35 according to the following relationship.

[Case of Scratch 33]

Luminous intensity signal of high-angle detection optical system 5a<luminous intensity signal of low-angle detection optical system 5b

[Case of Void 34]

Luminous intensity signal of high-angle detection optical system 5a>luminous intensity signal of low-angle detection optical system 5b

[Case of Particle 35]

Luminous intensity signal of high-angle detection optical system 5a≦luminous intensity signal of low-angle detection optical system 5b As shown above, when the luminous intensity signal of a defect is small, it is not possible to judge whether the defect is the small-sized particle 35 or large-sized scratch 33 using only one detection optical system, whereas it is possible to classify the defect by observing relative intensities of the luminous intensity signal of the high-angle detection optical system 5a and the luminous intensity signal of the low-angle detection optical system 5b.

In the example above, the classification of the scratch 33, void 34 and particle 35 on a semiconductor wafer has been explained, but it is also possible to classify a scratch or particle produced on, for example, a hard disk in a manufacturing process of the hard disk.

Figure 5:
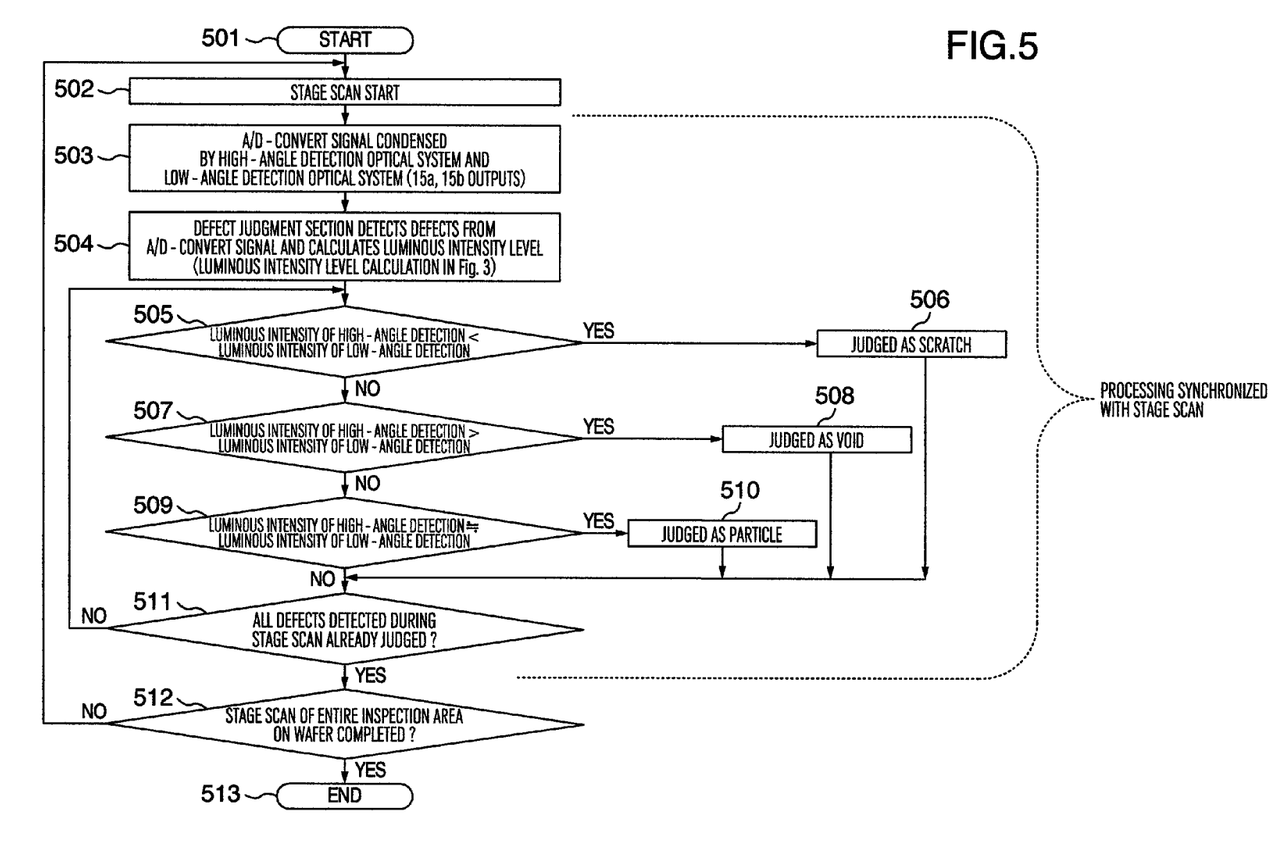
FIG. 5 is an example of a flowchart of classification according the embodiment of the present invention.

The above described classification will be explained by quoting the flowchart shown in FIG. 5.

The process starts in step 501 and a stage scan starts (step 502). Signals condensed by the high-angle detection optical system and low-angle detection optical system are A/D-converted (step 503). In step 504, defects are detected from the A/D-converted signals by the defect judgment section and their luminous intensity levels are calculated. In a comparison between the luminous intensity of high-angle detection and the luminous intensity of low-angle detection calculated (step 505), if the luminous intensity of high-angle detection<luminous intensity of low-angle detection, the defect is judged to be a scratch (step 506).

On the contrary, in the comparison between the luminous intensity of high-angle detection and the luminous intensity of low-angle detection calculated (step 507), if the luminous intensity of high-angle detection>luminous intensity of low-angle detection, the defect is judged to be a void (step 508).

On the other hand, in the comparison between the luminous intensity of high-angle detection and the luminous intensity of low-angle detection calculated (step 509), if the luminous intensity of high-angle detection≦luminous intensity of low-angle detection, the defect is judged to be a particle (step 510).

The above described judgment is repeated until all defects detected during stage scanning are judged. (step 511)

When repeated stage scanning on the entire area to be inspected on the wafer is completed (step 512), the process ends (step 513). Since the above described judgment is made in synchronization with stage scanning, the inspection process is speedily carried out.

Furthermore, since detection processes of the high-angle detection optical system and the low-angle detection optical system are carried out in parallel, this contributes to speed enhancement of the inspection.

The above described classification will be explained in further detail by quoting FIGS. 6 to 10.

Figure 6:
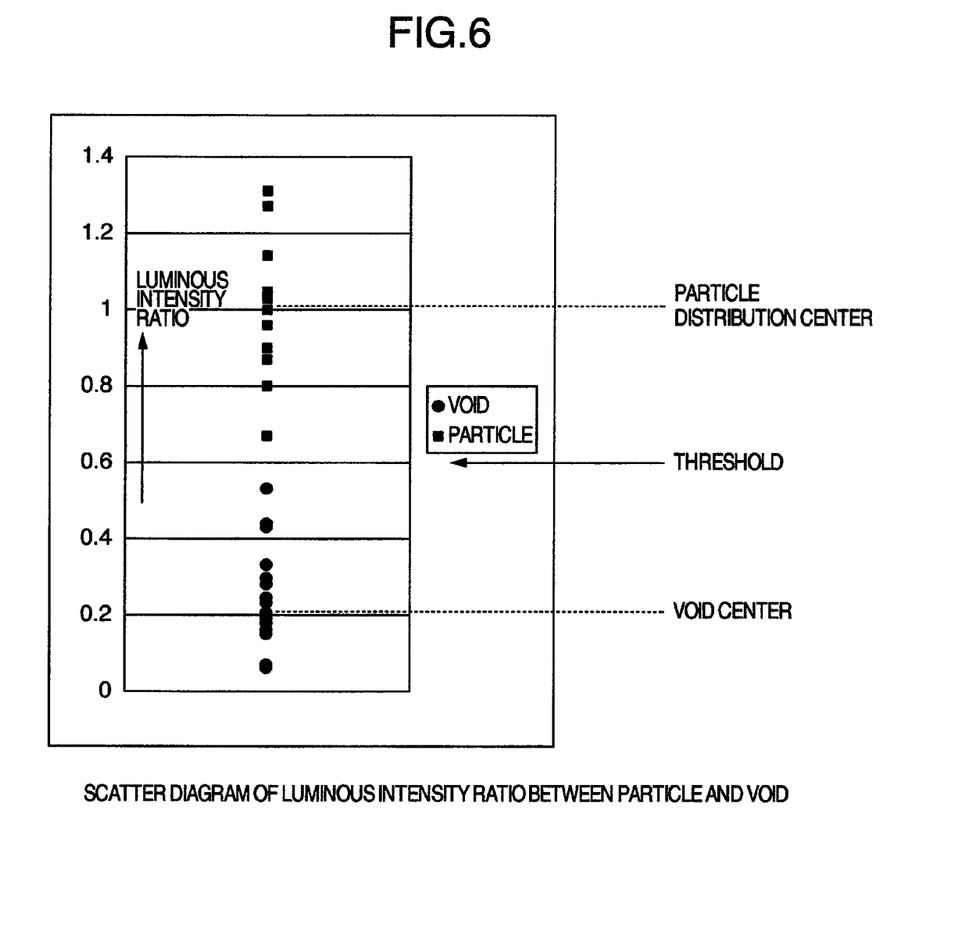
FIG. 6 is scatter diagram data of a luminous intensity ratio between particles and voids explained in the embodiment of the present invention.

FIG. 6 shows scatter diagram data of a luminous intensity ratio between particles and voids. This is a data example where the particle 35 and void 34 are actually classified.

The relative intensities of the luminous intensity signal of the high-angle detection optical system 5a and the luminous intensity signal of the low-angle detection optical system 5b are defined as the luminous intensity signal of the low-angle detection optical system 5b÷luminous intensity signal of the high-angle detection optical system 5a=luminous intensity ratio.

Assuming the threshold is 0.6 in the scatter diagram of the luminous intensity ratio, it is apparent that a defect equal to or greater than the threshold can be classified as the particle 35, a defect equal to or less than the threshold can be classified as the void 34. This threshold varies depending on the gain of each photoelectric transducer 7a, 7b, but the ability to classify defects based on a certain threshold is invariable irrespective of the size of the particle or void.

This principle will be explained using FIGS. 7 to 10.

Figure 7:
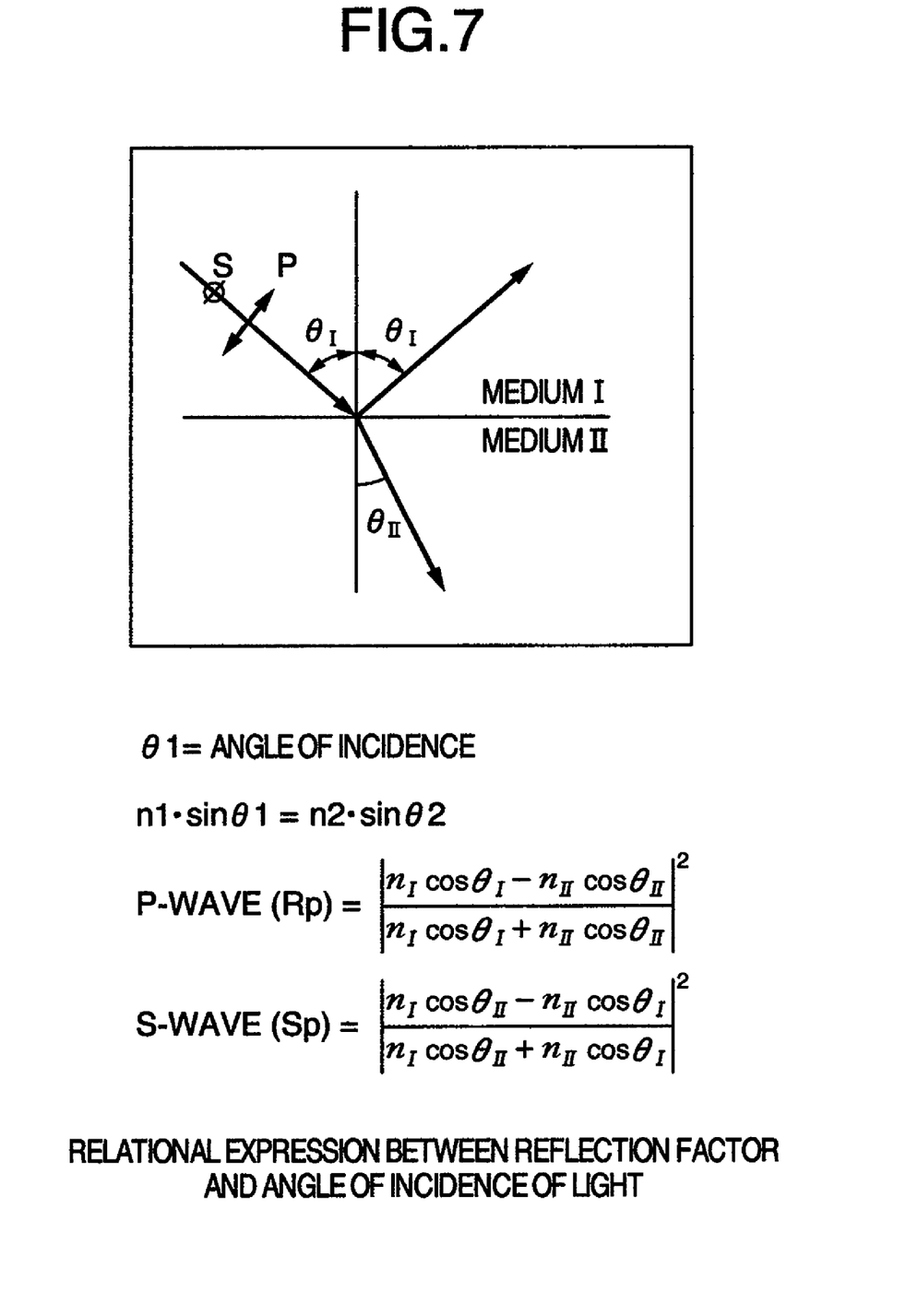
FIG. 7 is a relational expression between a reflection factor and an angle of incidence of light explained in the embodiment of the present invention.
Figure 8:
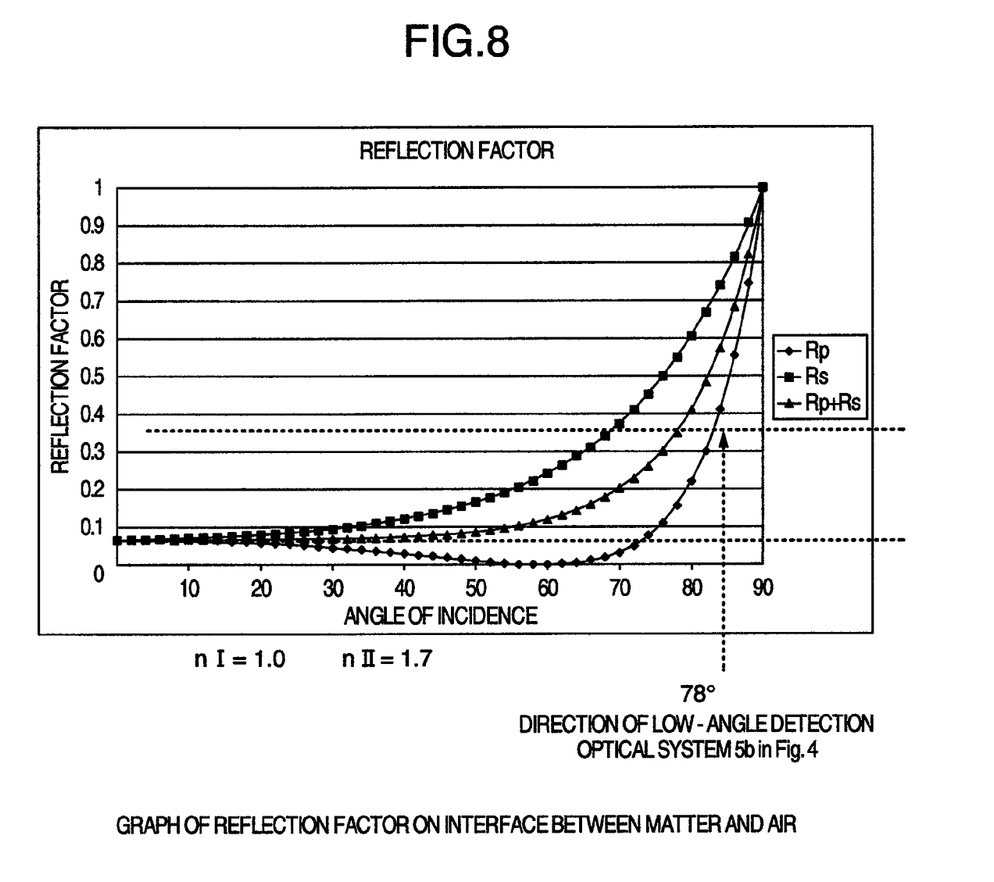
FIG. 8 is a graph showing the reflection factor and angle of incidence of light explained in the embodiment of the present invention.

FIG. 7 shows a general relational expression between a reflection factor and an angle of incidence of light on a certain plane. Here, P-wave (Rp) and S-wave (Rs) mean that an electric field vector of light is parallel and perpendicular to the plane of incidence respectively. FIG. 8 shows a graph of the reflection factor on an interface with n=1.7 between matter and air as an example. This graph is equal to a relationship when the numerical value (Expression 1) in the relational expression of FIG. 7 is assumed.

$$(nI=1.0, nII=1.7) \quad\quad\quad [\text{Expression 1}]$$

The shape of the graph generally varies depending on the refractive index of matter or the like, but the reflection factor increases as the angle of incidence of light approximates to parallel to the plane. When there is no polarization of the electric field vector of the incident light, the reflection factor of light becomes Rp+Rs of the graph. Furthermore, in FIG. 8, the angle perpendicular to the plane is assumed to be 0° and the angle parallel to the plane is assumed to be 90°. If this is applied to FIG. 4, (Scattering direction of high-angle detection optical system 5a in 90° direction . . . 0° direction in FIG. 8)

(Scattering direction of low-angle detection optical system 5b in 12° direction . . . 78° direction in FIG. 8)

The reflection factor "Rp+Rs" in FIG. 8 becomes approximately 0.07 at 0°. Furthermore, the reflection factor becomes 0.35 at 78°. The reflection factor increases approximately five-fold. There is also an approximately five-fold difference between the particle distribution center in FIG. 6 and void distribution center.

This principle will be explained when applied to the state where the scatter diagram data of the luminous intensity ratio in FIG. 6 is acquired.

Figure 9:
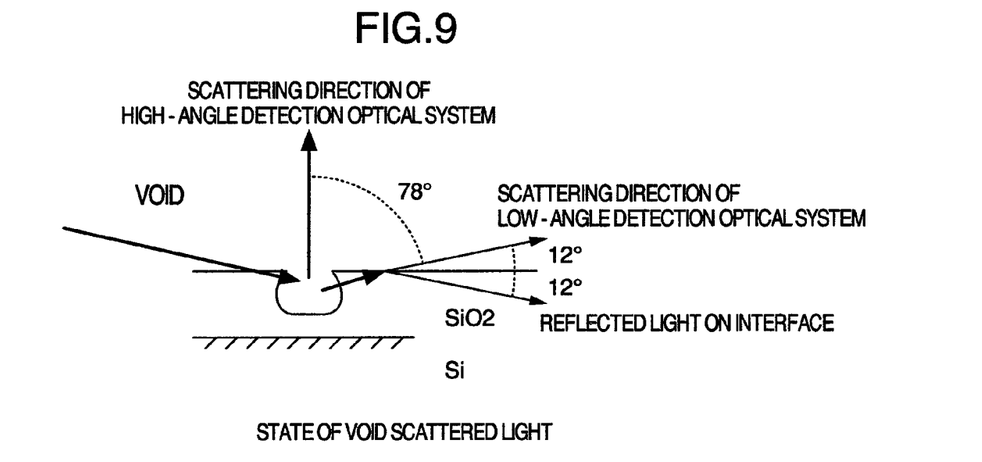
FIG. 9 shows a state of void scattered light explained in the embodiment of the present invention.

Like the state of the void scattered light shown in FIG. 9, there are not many blocking planes in the scattering direction of the high-angle detection optical system 5a in the 90° direction shown in FIG. 4. This direction corresponds to the 0° direction shown in FIG. 8.

On the contrary, there is an interface in the scattering direction of the low-angle detection optical system 5b in the 12° direction shown in FIG. 4, where there is a situation in which scattered light is significantly reflected, hardly reaching the low-angle detection optical system 5b. This direction becomes the 78° direction shown in FIG. 8. In this way, the luminous intensity ratio shown in FIG. 6 is assumed to decrease in the case of the void.

Figure 10:
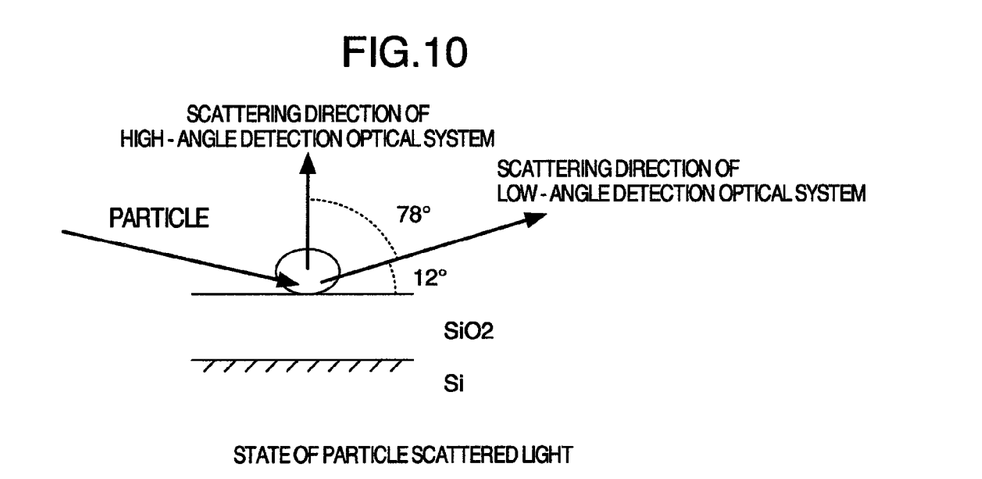
FIG. 10 shows a state of particle scattered light explained in the embodiment of the present invention.

On the other hand, in the state of the particle scattered light shown in FIG. 10, there is nothing that blocks in the scattering detection of the high-angle detection optical system 5a in the 90° direction or in the scattering detection of the low-angle detection optical system 5b in the 12° direction. This causes the luminous intensity ratio shown in FIG. 6 to increase in the case of the particle.

As described above, it is appreciated that keeping the angle of the low-angle detection optical system 5b to approximately 12° or below makes it possible to classify the particle and void.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An apparatus for inspecting an object, the apparatus comprising:
   an illumination system for illuminating the object;
   an optical detection system for detecting light from the object, the optical detection system including:
      a high-angle detection system orientated so as to have a high-angle with respect to the object, wherein said high-angle detection system acquires first information related to a luminous intensity of light detected by the high-angle detection system, and
      a low-angle detection system orientated so as to have a low-angle with respect to the object, wherein said low-angle detection system acquires second information related to a luminous intensity of light detected by the low-angle detection system, and
      a processing system for classifying each defect of the object based on a relationship between the first information and the second information, using at least one of following conditions:
         the defect is classified to be a void when the luminous intensity detected by the high-angle detection system is greater than the luminous intensity detected by the low-angle detection system,
         a defect is classified to be a scratch when the luminous intensity detected by the low-angle detection system is greater than the luminous intensity detected by the high-angle detection system, and
         a defect is classified to be a particle when the difference between the luminous intensity detected by the low-angle detection system and the luminous intensity detected by the high-angle detection system is not more than a predetermined value.

2. The apparatus according to claim 1, wherein the illumination system is an oblique illumination system.

3. The apparatus according to claim 2, wherein the high-angle detection system is arranged directly above a surface of the object, and the low-angle detection system and the illumination system are arranged within an angular range other than 0-45 degrees on an imaginary plane including X and Y axes of coordinates on a surface of the object.

4. The apparatus according to claim 2, wherein the illumination system is arranged within an elevation angle range of 3-20 degrees with respect to a surface of the object.

5. The apparatus according to claim 2, wherein the illumination system is arranged to have an elevation angle of about 12 degrees with respect to a surface of the object.

6. The apparatus according to claim 2, wherein the illumination system is arranged to have an elevation angle not more than 12 degrees with respect to a surface of the object.

7. An apparatus for inspecting an object, the apparatus comprising:
   an illumination system for illuminating the object;
   an optical detection system for detecting light from the object, the optical detection system including:
      a high-angle detection system orientated so as to have a high-angle with respect to the object, wherein said high-angle detection system acquires first information related to a luminous intensity of light detected by the high-angle detection system, and
      a low-angle detection system orientated so as to have a low-angle with respect to the object, wherein said low-angle detection system acquires second information related to a luminous intensity of light detected by the low-angle detection system, and
      a processing system for classifying each defect of the object based on a relationship between the first information and the second information, using at least one of following conditions:
         the defect is classified to be a void when the first information is greater than the second information,
         a defect is classified to be a scratch when the second information is greater than the first information, and
         a defect is classified to be a particle when the difference between the second information and the first information is not more than a predetermined value.

8. The apparatus according to claim 7, wherein the illumination system is an oblique illumination system.

9. The apparatus according to claim 8, wherein the high-angle detection system is arranged directly above a surface of the object, and the low-angle detection system and the illumination system are arranged within an angular range other than 0-45 degrees on an imaginary plane including X and Y axes of coordinates on a surface of the object.

10. The apparatus according to claim 8, wherein the illumination system is arranged within an elevation angle range of 3-20 degrees with respect to a surface of the object.

11. The apparatus according to claim 8, wherein the illumination system is arranged to have an elevation angle of about 12 degrees with respect to a surface of the object.

12. The apparatus according to claim 8, wherein the illumination system is arranged to have an elevation angle not more than 12 degrees with respect to a surface of the object.

13. A method for inspecting an object, the method comprising steps of:
   illuminating the object with an illumination system so that light from the object is detected by an optical detection system including:
      a high-angle detection system orientated so as to have a high-angle with respect to the object, wherein said high-angle detection system acquires first information related to a luminous intensity of light detected by the high-angle detection system, and
      a low-angle detection system orientated so as to have a low-angle with respect to the object, wherein said low-angle detection system acquires second information related to a luminous intensity of light detected by the low-angle detection system, and a processing step for classifying each defect of the object based on a relationship between the first information and the second information, using at least one of following conditions:

the defect is classified to be a void when the luminous intensity detected by the high-angle detection system is greater than the luminous intensity detected by the low-angle detection system, a defect is classified to be a scratch when the luminous intensity detected by the low-angle detection system is greater than the luminous intensity detected by the high-angle detection system, and a defect is classified to be a particle when the difference between the luminous intensity detected by the low-angle detection system and the luminous intensity detected by the high-angle detection system is not more than a predetermined value.

14. The method according to claim 13, wherein the illumination system is an oblique illumination system.

15. The method according to claim 14, wherein the high-angle detection system is arranged directly above a surface of the object, and the low-angle detection system and the illumination system are arranged within an angular range other than 0-45 degrees on an imaginary plane including X and Y axes of coordinates on a surface of the object.

16. The method according to claim 14, wherein the illumination system is arranged within an elevation angle range of 3-20 degrees with respect to a surface of the object.

17. The method according to claim 14, wherein the illumination system is arranged to have an elevation angle of about 12 degrees with respect to a surface of the object.

18. The method according to claim 14, wherein the illumination system is arranged to have an elevation angle not more than 12 degrees with respect to a surface of the object.

19. A method for inspecting an object, the method comprising steps of:

illuminating the object with an illumination system so that light from the object is detected by an optical detection system including:

a high-angle detection system orientated so as to have a high-angle with respect to the object, wherein said high-angle detection system acquires first information related to a luminous intensity of light detected by the high-angle detection system, and a low-angle detection system orientated so as to have a low-angle with respect to the object, wherein said low-angle detection system acquires second information related to a luminous intensity of light detected by the low-angle detection system, and a processing step for classifying each defect of the object based on a relationship between the first information and the second information, using at least one of following a defect is classified to be a scratch when the second information is greater than conditions:

the defect is classified to be a void when the first information is greater than the second information, the first information, and a defect is classified to be a particle when the difference between the second information and the first information is not more than a predetermined value.

20. The method according to claim 19, wherein the illumination system is an oblique illumination system.

21. The method according to claim 20, wherein the high-angle detection system is arranged directly above a surface of the object, and the low-angle detection system and the illumination system are arranged within an angular range other than 0-45 degrees on an imaginary plane including X and Y axes of coordinates on a surface of the object.

22. The method according to claim 20, wherein the illumination system is arranged within an elevation angle range of 3-20 degrees with respect to a surface of the object.

23. The method according to claim 20, wherein the illumination system is arranged to have an elevation angle of about 12 degrees with respect to a surface of the object.

24. The method according to claim 20, wherein the illumination system is arranged to have an elevation angle not more than 12 degrees with respect to a surface of the object.

* * * * *

UNITED STATES PATENT AND TRADEMARK OFFICE
CERTIFICATE OF CORRECTION

| | | |
|---|---|---|
| PATENT NO. | : 8,189,185 B2 | Page 1 of 1 |
| APPLICATION NO. | : 12/963416 | |
| DATED | : May 29, 2012 | |
| INVENTOR(S) | : Hideki Soeda et al. | |

It is certified that error appears in the above-identified patent and that said Letters Patent is hereby corrected as shown below:

Title Page item 57 Abstract should read:

An optical semiconductor wafer inspection system and a method thereof are provided for classifying and inspecting defects such as scratches, voids and particles produced in a flattening process by a polishing or grinding technique used for semiconductor manufacturing. The present invention is an optical semiconductor wafer inspection system and a method thereof characterized by obliquely illuminating a scratch, void or particle produced on the surface of a polished or ground insulating film at substantially the same velocity of light, detecting scattered light at the time of oblique illumination from the surface of an inspection target at different angles and thereby classifying the scratch, void or particle.

Signed and Sealed this
Nineteenth Day of February, 2013

Teresa Stanek Rea
*Acting Director of the United States Patent and Trademark Office*